United States Patent [19]

Kuhnis et al.

[11] 3,998,955
[45] Dec. 21, 1976

[54] ANTIHYPERTENSIVE COMPOSITIONS

[75] Inventors: Hans Kuhnis, Basel; Christian Egli, Magden; Kurt Eichenberger, Therwil; Phyllis Roberta Hedwall, Basel, all of Switzerland

[73] Assignee: Ciba-Geigy Corporation, Ardsley, N.Y.

[22] Filed: Apr. 16, 1975

[21] Appl. No.: 568,483

Related U.S. Application Data

[62] Division of Ser. No. 331,147, Feb. 9, 1973, Pat. No. 3,914,239.

[52] U.S. Cl. .............................. 424/266; 424/263
[51] Int. Cl.² ..................................... A61K 31/455
[58] Field of Search ........................... 424/263, 266

[56] References Cited

UNITED STATES PATENTS 3,862,159  1/1975  Umezawa et al. ................ 424/266

FOREIGN PATENTS OR APPLICATIONS 1,219,176  1/1971  United Kingdom ........... 260/295 R

OTHER PUBLICATIONS

Markees et al., Chemical Abstracts 51:2775–2777, 1/10/57.
Cutting, Handbook of Pharmacology, 4th Edition, (1969) pp. 286–287.

*Primary Examiner*—Norman A. Drezin
*Attorney, Agent, or Firm*—Joseph G. Kolodny; John J. Maitner; Theodore O. Groeger

[57] ABSTRACT

Pyridines of the formula I

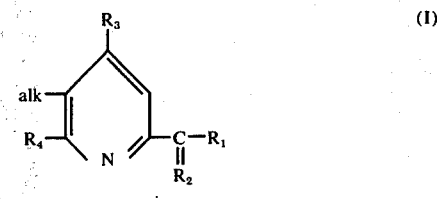

wherein $R_1$ is free hydroxyl, lower alkoxy, cycloalkoxy, amino-lower alkoxy or lower alkoxy-lower alkoxy, free amino, hydroxyamino, lower alkyleneamino, oxa-, aza- or thia-lower alkyleneamino or mono- or di-lower alkylamino, $R_2$ is oxygen or sulphur, $R_3$ and $R_4$ are each alkoxy, free amino, mono- or di-lower alkylamino, lower alkyleneamino, oxa-, aza- or thia-lower alkyleneamino, halogen or free hydroxyl, and either $R_3$ or $R_4$ can be hydrogen, and alk is an alkyl group with 3–10 carbon atoms, and their N-oxides, and salts are useful as dopamine-β-hydroxylase inhibitors.

7 Claims, No Drawings

ANTIHYPERTENSIVE COMPOSITIONS

This is a division of application Ser. No. 331,147, now U.S. Pat. No. 3,914,239.

The present invention relates to new pyridine compounds of the formula I

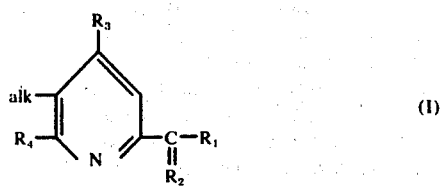

wherein alk is an alkyl group with more than two carbon atoms, $R_1$ is an optionally substituted hydroxyl group or an optionally substituted amino group, $R_2$ is oxygen or sulphur and $R_3$ and $R_4$ independently of one another are an alkoxy group, an optionally substituted amino group, a halogen or a hydroxyl group, and either $R_3$ or $R_4$ can be hydrogen, as well as their salts and N-oxides and processes for their manufacture.

In the preceding and following text, alkyl groups alk are understood as branched or above all straight-chain alkyl radicals with 3–10 carbon atoms, preferably lower alkyl radicals with 4–6 carbon atoms, and very particularly lower alkyl radicals with 4 and 5 carbon atoms. Examples of such lower alkyl radicals are propyl and isopropyl radicals and straight and branched butyl, pentyl, hexyl, heptyl, octyl, nonyl and decyl radicals bonded in any desired position.

An optionally substituted hydroxyl group $R_1$ is, for example, an etherified, hydroxyl group, such as a hydroxyl group substituted by lower alkyl groups or cycloalkyl groups or azaalkyl or oxaalkyl groups, that is to say lower alkoxy, cycloalkoxy, azaalkoxy or oxaalkoxy, but also free hydroxyl.

The lower alkyl part of a lower alkoxy group $R_1$ is a branched and preferably straight-chain lower alkyl group, preferably with 1–7 carbon atoms and especially with 1–3 carbon atoms, such as, for example, methyl, ethyl, propyl and isopropyl, and straight-chain or branched butyl, pentyl, hexyl or heptyl bonded in any desired position.

A cycloalkoxy group $R_1$ is, for example, a cycloalkoxy group wherein the cycloalkyl part has 3–8, especially 3–6, ring carbon atoms. Examples of such radicals are cyclohexoxy, cyclopentoxy, cyclobutoxy and cyclopropoxy.

Azaalkyl and oxaalkyl groups in azaalkoxy and oxaalkoxy groups $R_1$ are especially optionally substituted aminoalkyl or alkoxyalkyl groups, respectively, wherein the lower alkyl part preferably contains 1–7 carbon atoms and especially 1–3 carbon atoms. Azaalkoxy groups $R_1$ are, for example, amino-lower alkoxy, mono- or di-lower alkylamino-lower alkoxy or lower alkyleneamino-lower alkoxy, preferably with up to 7 C atoms, such as aminomethoxy, methylaminomethoxy, 2-methylaminoethoxy, 2-dimethylaminoethoxy, methoxymethoxy, ethoxymethoxy, 2-ethoxyethoxy, 2-methoxyethoxy, propoxymethoxy, 3-methoxypropoxy, pyrrolidino-methoxy or 2-piperidinoethoxy.

Oxaalkoxy $R_1$ is especially lower alkoxyalkoxy, wherein lower radicals are in particular those with 1–7 C atoms, such as ethoxymethoxy, propoxymethoxy and especially methoxymethoxy 2-methoxy-ethoxy and 3-methoxypropoxy.

Optionally substituted amino groups $R_1$ are, for example, mono- and di-lower alkylamino groups, lower alkyleneamino groups in which the lower alkylene part can also be interrupted by hetero-atoms, such as oxygen, sulphur or nitrogen, and/or substituted, for example, substituted by hydroxyl, and hydoxyamino groups.

Mono- and di-lower alkylamino $R_1$ in particular possesses 1–7, above all 1–3, C atoms in the lower alkyl part. Lower alkyleneamino in particular has up to 7 C atoms and preferably at least 2 C atoms in the lower alkylene part, above all 4 or 5 C atoms in the alkylene chain, such as butylene-1,4, pentylene-1,5, 1,5-dimethylpentylene-1,5, hexylene-1,6 and hexylene-1,5. Thus, for example, $R_1$ is free amino, methylamino, ethylamino, n-propylamino, dimethylamino, diethylamino, di-n-propylamino, N-methyl-N-ethylamino, pyrrolidino or piperidino.

Lower alkyleneamino $R_1$ interrupted by heteroatoms is, for example, oxa-, thia- and aza-lower alkyleneamino, such as morpholino, thiomorpholino, 2,6-dimethylthiomorpholino, piperazino, 2,6-dimethylpiperazino, N'-methyl-piperazino or N'-(2-hydroxyethyl)-piperazino.

Halogen represents fluorine and bromine and especially chlorine.

The new pyridine compounds possess valuable pharmacological properties.

Thus they display a dopamine-β-hydroxylase inhibition, as can be shown on rats in doses of about 20 to about 500 mg/kg administered orally, and an antihypertensive action, as can be shown on renal hypertonic rats and metacortacoid-salt hypertonic rats in doses of about 20 to about 100 mg/kg/day, administered orally, and on renal hypertonic dogs in doses of about 20 to about 100 mg/kg/day, administered orally. The new compounds are therefore useful as dopamine-β-hydroxylase inhibitors having an anti-hypertensive action and surprisingly good toleration. The new compounds can furthermore serve as intermediate products for the manufacture of other useful substances, especially pharmaceutically active compounds.

Particularly valuable compounds of the formula I are those wherein $R_1$ is free hydroxyl, lower alkoxy, cycloalkoxy, amino-lower alkoxy or lower alkoxy-lower alkoxy, free amino, hydroxyamino, lower alkyleneamino, oxa-, aza- or thia-lower alkyleneamino, or mono- or di-lower alkylamino, $R_2$ is oxygen or sulphur, $R_3$ and $R_4$ are each alkoxy, free amino, mono- or di-lower alkylamino, lower alkyleneamino, oxa-, aza- or thia-lower alkyleneamino, halogen or free hydroxyl, and either $R_3$ or $R_4$ can be hydrogen, and alk is an alkyl group with 3–10 carbon atoms, as well as their N-oxides.

Particularly suitable compounds of the formula I amongst those which have been mentioned are those wherein $R_1$ is free hydroxyl, lower alkoxy, free amino, hydroxyamino, mono-lower alkylamino, di-lower alkylamino, pyrrolidino, piperidino, morpholino, thiomorpholino, 2,6-dimethylthiomorpholino, piperazino, N'-methyl-piperazino or N(-(2-hydroxyethyl)-piperazino and $R_2$ is oxygen, or wherein the group $-C(=R_2)R_1$ is thiocarbamoyl, $R_3$ and $R_4$ are each alkoxy, free amino, mono-lower alkylamino, di-lower alkylamino, pyrrolidino, piperidino, morpholino, thiomorpholino, piperazino, halogen or free hydroxyl, and one of the radicals $R_3$ and $R_4$ can also be hydrogen, and alk is an alkyl group with 4 or 5 carbon atoms, as well as their salts.

Amongst these compounds, there are especially to be singled out those of the formula I wherein $R_1$ is free hydroxyl, methoxy, ethoxy, free amino, methylamino, dimethylamino, ethylamino, diethylamino, pyrrolidino, piperidino, morpholino, thiomorpholino or piperazino, $R_2$ is oxygen, $R_3$ and $R_4$ are each methoxy, ethoxy, free amino, methylamino, dimethylamino, ethylamino, diethylamino, pyrrolidino, piperidino, morpholino, chlorine or free hydroxyl, and one of the radicals $R_3$ and $R_4$ can also be hydrogen, and alk is an alkyl group with 4 or 5 carbon atoms, with alk in particular having a straight chain.

Individually, there should be mentioned: 2-carboxy-4,6-dichloro-5-n-butyl-pyridine, 2-carboxy-4-methoxy-5-n-butyl-6-chloro-pyridine, 2-carboxy-4-methoxy-5-n-butyl-pyridine, 2-carboxy-4-chloro-5-n-butyl-6-methoxy-pyridine, 2-methoxycarbonyl-5-n-butyl-6-methoxy-pyridine, 2-carboxy-5-n-butyl-6-methoxy-pyridine, 2-methoxycarbonyl-4-chloro-5-n-butyl-6-amino-pyridine, 2-methoxycarbonyl-5-n-butyl-6-amino-pyridine, 2-methoxycarbonyl-4-methoxy-5-n-butyl-pyridine, 2-carbamoyl-4-methoxy-5-n-butyl-pyridine, 2-carboxy-4-n-propoxy-5-n-butyl-pyridine, 2-carboxy-4-methoxy-5-isoamyl-pyridine, 2-carboxy-4-methoxy-5-n-amyl-pyridine, 2-carboxy-4-ethoxy-5-n-butyl-pyridine, 2-methoxycarbonyl-4-piperidino-5-n-butyl-6-chloro-pyridine, 2-methoxycarbonyl-4-piperidino-5-n-butyl-pyridine, 2-carboxy-4-methoxy-5-n-butyl-6-piperidino-pyridine, 2-carboxy-4,6-dimethoxy-5-n-butyl-pyridine and 2-methoxycarbonyl-4-chloro-5-n-butyl-6-hydroxy-pyridine.

2-Carboxy-4-methoxy-5-n-butyl-pyridine, which in rats shows a dopamine-$\beta$-hydroxylase inhibition in doses of 30–500 mg/kg administered orally, and an anti-hypertensive action, coupled with good toleration, in renal hypertonic rats, should be mentioned especially.

The new pyridine compounds are obtained according to methods which are in themselves known.

Thus, for example, a possible procedure is that a compound of the formula

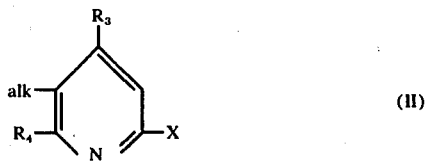

wherein alk, $R_3$ and $R_4$ have the above meaning, or a hydrate thereof or a N-oxide thereof, is oxidised.

The oxidation can be carried out in the customary manner. Suitable oxidising agents are weak, medium-strength or strong oxidising agents, such as atmospheric oxygen, if appropriate in the presence of catalytic amounts of heavy metals, for example manganese, platinum or palladium, or heavy metal salts, such as manganese salts, for example manganese-II sulphate, or of peroxides, such as acyl peroxides, for example diacetyl peroxide, or inorganic oxidising oxygen compounds such as permanganates, for example calcium permanganate, nitrates, for example potassium nitrate, nitric acid, chromates, for example potassium chromate or potassium dichromate, if appropriate together with an acid, such as sulphuric acid, and hydrogen peroxide, if appropriate together with alkali, such as sodium hydroxide solution or potassium hydroxide solution. Oxidation, can be carried out particularly gently with, for example, silver oxide $Ag_2O$, for example as a suspension in alkali, such as sodium hydroxide solution or potassium hydroxide solution, or in ammoniacal solution. The oxidation can also be carried out electrolytically in the customary manner.

If appropriate, sensitive functional groups are protected for the duration of the oxidation, for example in the customary manner. Thus, hydroxyl groups and/or amino groups can be acylated in the customary manner. Thereafter, when the oxidation has been carried out, the compounds with hydroxyl groups and/or amino groups can be liberated from the acylated oxidised compounds in the customary manner. The type of acylation is here of secondary importance. Suitable acyl protective groups are, for example, alkanoyl, such as acetyl, or aroyl, such as benzoyl. Further examples of suitable protective groups are those indicated below.

In compounds obtained, substituents can be introduced, modified or split off within the framework of the definition of the final substances.

Esterified carboxyl groups, carbamoyl groups and thiocarbamoyl groups can be converted into free carboxyl groups in the customary manner, for example by hydrolysis, preferably in the presence of strong bases, such as alkali metal hydroxides, for example sodium hydroxide or potassium hydroxide, or strong acid, such as hydrochloric acid or sulphuric acid. If desired, oxidising agents, such as nitrous acid, can be added during the hydrolysis of carbamoyl groups and thiocarbamoyl groups.

Esterified carboxyl groups and carbamoyl groups can also be reacted in the customary manner with hydroxylamine to give hydroxamic acids, advantageously in the presence of an alcohol, such as methanol or ethanol, or of an acid, preferably hydrochloric acid.

Free or esterified carboxyl groups can also be converted into carbamoyl groups in the customary manner, for example by reaction with ammonia or with amines possessing at least one hydrogen atom on the nitrogen atom, and, if necessary, dehydration of the ammonium salt produced as an intermediate.

Free carboxyl groups can be esterified in the customary manner, for example by reaction with an appropriate alcohol, advantageously in the presence of an acid, such as a mineral acid, for example sulphuric acid or hydrochloric acid, or in the presence of a water-binding agent, such as dicyclohexylcarbodiimide, or by reaction with an appropriate diazo compound, for example a diazoalkane. The esterification can also be carried out by reaction of a salt of the acid, for example the sodium salt, with a relatively esterified alcohol, for example a corresponding halide, such as a chloride.

Carboxyl groups substituted by hydroxylamine can be converted into free carboxyl groups by hydrolysis in a manner which is in itself known, for example as described above.

Furthermore, thiocarbamoyl groups can be converted into the corresponding carbamoyl groups by hydrolysing the thiamide group, such as by treatment with water, if appropriate in the presence of oxidising agents, such as hydrogen peroxide or nitrous acid, or of sulphur-binding agents, such as lead oxide or mercury oxide.

In resulting compounds wherein $R_3$ and/or $R_4$ are hydroxyl groups, these can be etherified in the customary manner, for example by reaction with a reactive ester of the alkanol in question, preferably in the presence of a basic condensation agent, for example an alkali metal hydroxide, such as sodium hydroxide, or especially with a diazoalkane, such as diazomethane. Where applicable, especially in the reaction with a diazoalkane, there may be produced, alongside the desired etherified hydroxy compounds, compounds in which the attack of the etherifying agent has taken place at a N-oxide group which may be present, and the compounds according to the invention then have to be separated from these compounds in the customary manner.

In resulting compounds which possess alkoxy groups, these groups can be converted in the customary manner into hydroxyl groups, for example by means of hydrobromic acid or hydriodic acid.

Furthermore, a pyridine compound of the formula I can be N-oxidised. The oxidation is carried out in the customary manner, for example with N-oxidising agents, such as hydrogen peroxide, ozone, inorganic per-acids, for example persulphuric acids, such as Caro's acid, or especially organic peroxy compounds, above all organic peracids, such as peracetic acid, petrifluoroacetic acid, perbenzoic acid or monoperphthalic acid, which can also be substituted, for example by halogen atoms, such as chlorine atoms, for example chloromonoperphehalic acid or m-chloroperbenzoic acid, or tertiary hydroperoxide compounds, such as tert.butyl peroxide or cumene peroxide, optionally in the presence of catalysts, such as vanadium, titanium or molybdenum compounds.

Resulting pyridine-N-oxide compounds can be converted into the corresponding pyridine compounds by reduction. The reduction is carried out in the customary manner, advantageously catalytically, as described below, or by the action of phosphorus halides.

If necessary, free hydroxyl groups can be transiently protected, for example by etherification with hydrogenolytically removable groups, such as benzyl groups, or esterification with hydrolytically removable acids, such as organic carboxylic acids or sulphonic acids and can, if desired, be liberated after carrying out the reaction, for example hydrogenolytically (such as by treatment with hydrogen in the presence of a metal catalyst, such as a palladium catalyst) or hydrolytically (such as by treatment with a suitable basic hydrolysis agent). In the hydrogenolytic splitting off, reaction times which are as short as possible and conditions which are as mild as possible should be chosen in order not to attack any N-oxide groups which may be present. In cases where N-oxide groups are present, palladium on charcoal and hydrogen at room temperature, with a short reaction time, is a particularly suitable combination.

In resulting compounds which contain a mono- or di-lower alkylamino group or a lower alkyleneamino group, these groups can be converted into a free amino group by oxidative splitting off. The oxidative splitting off can be carried out in the customary manner, for example with a strong inorganic oxidising agent, such as potassium permanganate, especially in a protonic solvent, such as an alcohol, for example a lower alkanol, or above all water.

In resulting compounds which contain a halogen atom, the latter can be split off by reduction, for example in the customary manner with hydrogen in the presence of a catalyst, such as a heavy metal catalyst, for example platinum, palladium or nickel, such as palladium on active charcoal or Raney nickel. For this, reaction times which are as short as possible are chosen in order not to attack any N-oxide groups which may be present. In cases where N-oxide groups are present, palladium on active charcoal and hydrogen at room temperature, with a short reaction time, is a particularly suitable combination.

In resulting compounds which contain a halogen atom, the latter can be converted into a primary amino group by treatment with, for example, ammonia, or into a substituted amino group by treatment with an amine, in the usual manner.

In resulting compounds which contain halogen atoms, these can be converted in the usual manner into hydroxyl or alkoxy groups, for example by treatment with suitable bases, such as alkali metal hydroxides, for example sodium hydroxide, or alcoholates, such as sodium alkanolates, for example sodium ethylate or sodium methylate.

In resulting compounds which possess at least one hydrogen atom on an amino group, this atom can be substituted. The substitution is effected, for example, by reaction with a reactive ester of an appropriate alcohol, such as one of those mentioned above. The reaction takes place in the customary manner, advantageously in the presence of a basic condensation agent, such as an alkali metal hydroxide, for example sodium hydroxide or potassium hydroxide.

The subsequent conversions can be carried out individually or in combination and in any desired sequence. Care must be taken in the individual operations that other functional groups are not attacked.

The reactions mentioned are carried out in the customary manner, preferably in the presence of solvents, at ordinary, lowered or raised temperature and, if appropriate, in a closed vessel under pressure.

The invention also relates to those embodiments of the process in which the process is stopped at any stage or in which a compound obtainable as an intermediate product at any stage is used as the starting product and the missing steps, for example the N-oxidation, are carried out, or a starting substance is formed under the reaction conditions or is used, if relevant, in the form of a salt and/or racemate or optical antipode.

Thus it is possible to oxidise a compound of the formula III

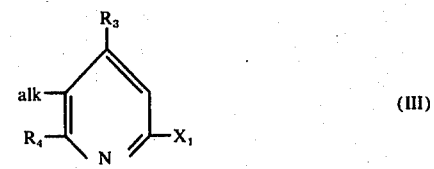

wherein $R_3$, $R_4$ and alk have the above meanings and $X_1$ represents methyl, hydroxymethyl, halogeno-methyl vinyl or styryl. Herein, a compound of the formula II is obtained as an intermediate and this then reacts further according to the invention.

The oxidation can be carried out in the customary manner, especially by strong oxidising agents, such as permanganates, for example potassium permanganate, or by chromates, such as potassium chromate, optionally in the presence of acid, such as sulphuric acid, nitrates, for example potassium nitrate, nitric acid, peracids, for example persulphuric acid, or selenium dioxide, optionally in an organic solvent, such as pyridine, benzene, toluene or dioxane.

In the above reactions functional groups are optionally protected as indicated above.

Depending on the process conditions and the starting substances, the basic final substances are obtained in the free form or in the form of their acid addition salts which is also included in the invention. Thus, for example, basic, neutral or mixed salts and possibly also hemihydrates, monohydrates, sesquihydrates or polyhydrates thereof, can be obtained. The acid addition salts of the new compounds can be converted in a manner which is in itself known into the free compounds, for example with basic agents, such as alkalis or ion exchangers. On the other hand, the resulting free basis can form salts with organic or inorganic acids. To manufacture acid addition salts, those acids which are suitable for forming therapeutically usable salts are, in particular, employed. As examples of such acids there may be mentioned: hydrogen halide acids, sulphuric acids, phosphoric acid, nitric acid, perchloric acid, aliphatic, alicyclic, aromatic or heterocyclic carboxylic or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid and ethylenesulphonic acid; halogenobenzenesulphonic acid, toluenesulphonic acid, naphthalenesulphonic acid or sulphanilic acid; methionine, tryptophane, lysine or arginine.

Acid final substances can also, depending on the process conditions and starting substances, be obtained in the free form or in the form of their salts which is also included in the invention. Resulting free acids can be converted in the customary manner, for example by reaction with appropriate basic agents, into the salts with bases, above all into therapeutically usable salts with bases, for example salts with organic amines or metal salts. Possible metal salts are above all alkali metal salts or alkaline earth metal salts, such as sodium, potassium, magnesium or calcium salts. Free acids can be liberated from salts in the customary manner, for example by reaction with acid agents.

These or other salts of the new compounds such as, for example, the picrates, can also be used for purifying the resulting free bases, by converting the free bases into salts, isolating the latter and again liberating the bases from the salts. Because of the close relationships between the new compounds in the free form and in the form of their salts the free compounds are to be understood, in the preceding and following text, where appropriate also to include the corresponding salts, in general sense and intended use.

Depending on the number of the asymmetrical C atoms and the choice of the starting substances and procedures, the new compounds can be in the form of racemate mixtures, racemates or optical antipodes.

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which form salts with the racemic compound and separation of the salts obtained in this manner, for example on the basis of their different solubilities, into the diastereomers from which the antipodes can be liberated by the action of suitable agents. Particularly customary optically active acids are, for example, the d- and α-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure racemates or optical antipodes.

Preferably, those starting substances which lead to the final substances which have initially been particularly singled out are employed for carrying out the reactions according to the invention.

The starting substances are known or can, if they are new, be obtained according to methods which are in themselves known. New starting substances are in particular those of the formula

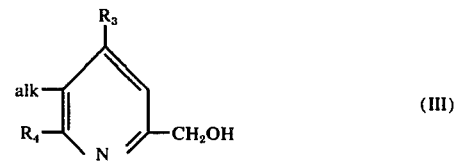

wherein $R_3$, $R_4$ and alk have the above general meaning and especially the meaning singled out, and which have the same pharmacological properties as the compounds of the formula I.

In particular, 2-hydroxymethyl-4-methoxy-5-n-butyl-pyridine, 2-hydroxymethyl-4-methoxy-5-n-butyl-6-chloropyridine and 2-hydroxymethyl-4-chloro-5-n-butyl-6-piperidinopyridine should be singled out.

The compounds of the formula III can be obtained according to methods which are in themselves known.

Compounds of the formula III can be manufactured by rearrangement from the appropriately substituted 2-methyl-pyridine-N-oxides. The rearrangement is carried out, for example, in the presence of anhydrides at elevated temperatures, preferably at temperatures between 80° and 180°, followed by hydrolysis. Amongst the anhydrides, acetic anhydride, trifluoroacetic anhydride and propionic anhydride should be mentioned particularly. The esters formed are preferably hydrolysed in the presence of acids, in accordance with known methods. Mixtures of anhydrides with acids, such as, for example, trifluoroacetic acid and trifluoroacetic anhydride, can also be used equally well. The alcohols can be manufactured directly in this manner.

It is furthermore possible to manufacture compounds of the formula III by hydrolysing a compound of the formula IV

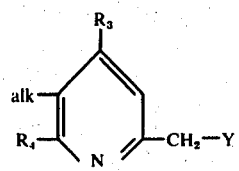

(IV)

wherein alk, $R_3$ and $R_4$ have the above meaning and Y is an esterified hydroxyl group, for example one of those mentioned above or a hydroxyl group esterified by a radical of an organic acid, such as an alkylcarboxylic acid, for example acetic acid, or an arylcarboxylic acid, for example benzoic acid. The hydrolysis can be carried out in the customary manner, for example as described above.

A further possibility for the manufacture of compounds of the formula III is the reduction of compounds of the formula I in which $R_2$ is oxygen and $R_1$ is the hydroxyl group. This reduction is advantageously carried out with complex hydrides, such as, for example, lithium aluminium hydride.

The new, pharmacologically active compounds can be used, for example, in the form of pharmaceutical preparations in which they are present in the free form or, optionally, in the form of their salts, especially of the therapeutically usable salts, mixed with a pharmaceutical, organic or inorganic, solid or liquid excipient suitable, for example, for enteral or parenteral administration. Suitable substances for forming the excipient are those which do not react with the new compounds, such as, for example, water, gelatine, lactose, starch, stearyl alcohol, magnesium stearate, talc, vegetable oils, benzyl alcohols, gum, propylene glycols, white petroleum jelly or other known medicinal excipients. The pharmaceutical preparations can, for example, be in the form of tablets, dragees, capsules or suppositories or in a liquid form as solutions (for example as an elixir or syrup), suspensions or emulsions. They are optionally sterilised and/or contain auxiliaries, such as preservatives, stabilisers, wetting agents or emulsifiers, solubilising agents or salts for regulating the osmotic pressure or buffers. They can also contain other therapeutically valuable substances. The pharmaceutical preparations are formulated in accordance with customary methods. The dosage of the new compounds can vary depending on the compound and on the individual requirements of the patient.

The new, pharmacologically active compounds can also be used in veterinary medicine, for example in one of the abovementioned forms or in the form of feedstuffs or of additives to animal fodder. For this, for example, the customary extenders and diluents are used.

The invention furthermore also relates to pharmaceutical preparations for the treatment of hypertonia, containing a combination of an anti-hypertensively active aminoacid and a compound of the formula I, especially one of those which have been singled out.

Anti-hypertensively active aminoacids are, for example, α-methyl-p-tyrosine and above all compounds of the type of α-methyldopa.

Anti-hypertensively active aminoacids, above all compounds of the type of α-methyldopa, especially α-methyldopa itself, have proved very successful in the therapy of hypertonia. Thus, α-methyldopa is used successfully in practically all forms of hypertonia in a dosage of about 0.5 g to about 2 g, and at times even up to about 4 g, per day, compare E. Mutschler, Arzneimittelwirkungen (Effects of Medicaments), Wissenschaftliche Verlagsgesellschaft mbH, Stuttgart 1970, page 134.

Surprisingly, it has now been found that by treating hypertonia with a combination of an anti-hypertensively active aminoacid and a compound of the formula I the anti-hypertensive action can be prolonged and made more uniform and the dosage of the components, that is to say of the anti-hypertensively active aminoacid and of the compound I, can be reduced, as can be shown on oral or subcutaneous administration of customary component doses to male, renal hypertonic rats in accordance with the method of Goldblatt. The anti-hypertensive action here proves to be substantially longer-lasting than would correspond to the sum of the anti-hypertensive actions of the active substance components.

This prolongation of the anti-hypertensive action makes it possible to manage with a single daily administration of the combination preparation according to the invention. The essentially more uniform action of lowering the blood pressure substantially reduces the disadvantages of a fluctuation in blood pressure over the course of the day, as occurs in the known treatment of hypertonia by means of the individual active substance components, and makes the therapy more even and more easily tolerated for the patient. The reduction of the component doses reduces the hazards of an overdose and is especially of advantage because of the known high doses of the anti-hypertensively active aminoacids, especially of the compounds of the type of α-methyldopa, so that a general reduction of the stress on the organism of the patient can be achieved.

Possible compounds of the type of α-methyldopa are above all α-amino-α-methyl-β-hydroxyphenyl-propionic acids, their salts and esters.

Salts are especially salts with bases, such as alkali metal carbonates, for example sodium carbonate or potassium carbonate, alkali metal bicarbonates, alkali metal hydroxides, such as sodium hydroxide or potassium hydroxide, or corresponding alkaline earth metal compounds, such as those of calcium or magnesium, or ammonia, as well as amines, such as aliphatic amines, for example lower alkylamines, such as trimethylamine or triethylamine, as well as aluminium compounds, such as aluminium hydroxide, for example salts of two mols of acid and one mol of aluminium hydroxide, which are suitable in particular because of their slower resorption, absence of odour and low gastro-intestinal disturbances.

Esters are above all lower alkyl esters, such as methyl esters and ethyl esters. Lower radicals are, in the preceding and following texts, above all those with up to 7, preferably with up to 4, C atoms.

Compounds to be singled out particularly are α-amino-α-methyl-β-(4-hydroxyphenyl)-propionic acid and very particularly α-amino-α-methyl-β-(3,4-dihydroxyphenyl)propionic acid, which is known under the name of α-methyldopa, as well as their salts, such as, in particular, their alkali metal or alkaline earth metal salts and, secondly, their esters, such as lower alkyl esters.

The active substances mentioned can, depending on the number of their asymmetrical carbon atoms, be in the form of isomer mixtures, pure isomers (racemates) or optical antipodes. Preferably, they are in each case used in the form of the more active or less toxic isomer or antipode. For example, its laevo-rotatory antipode can preferably be used as α-methyldopa.

Active substances with basic groups, especially esters of the type of α-methyldopa, can be present in the free form or in the form of their non-toxic salts. As such salts, it is possible to use, in particular, salts with organic or inorganic acids, such as hydrogen halide acids, sulphuric acid, phosphoric acids, nitric acid, perchloric acid, aliphatic, alicyclic, aromatic or heterocyclic carboxylic or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid and ethylenesulphonic acid; halogenobenzenesulphonic acid, toluenesulphonic acid, naphthalenesulphonic acid or sulphanilic acid; cyclohexylsulphamic acid, methionine, tryptophane, lysine or arginine.

The invention relates both to pharmaceutical preparations containing a combination of an anti-hypertensively active aminoacid, especially of one of those mentioned above as being preferred, and a compound I, especially one of those mentioned above as being preferred, and to the manufacture of such preparations as well as to the use of the active substances in the form of the said preparations or by combined but separate administration for the treatment of hypertonia.

Pharmaceutical preparations to be particularly singled out are those which contain, as the anti-hypertensively active aminoacid, α-amino-α-methyl-β-(4-hydroxyphenyl)-propionic acid or α-amino-α-methyl-β-(3,4-dihydroxyphenyl)-propionic acid or a salt or a lower alkyl ester thereof, and as the compound I a compound wherein $R_1$ is free hydroxyl, methoxy, ethoxy, free amino, methylamino, dimethylamino, ethylamino, diethylamino, pyrrolidino, piperidino, morpholino, thiomorpholino or piperazino, $R_2$ is oxygen, $R_3$ and $R_4$ are each methoxy, ethoxy, n-propoxy, free amino, methylamino, dimethylamino, ethylamino, diethylamino, chlorine or free hydroxyl and one of the radicals $R_3$ and $R_4$ can also be hydrogen, and alk is a straight-chain alkyl group with 4 or 5 carbon atoms, or a salt thereof.

The invention however above all relates to pharmaceutical preparations containing α-amino-α-methyl-β-(3,4-dihydroxyphenyl)-propionic acid or a non-toxic salt thereof and 2-carboxy-4-methoxy-5-n-butyl-pyridine or a non-toxic salt thereof.

Correspondingly, the use of these preferred preparations or the use of the individual components in a combination therapy is also a particular subject of the invention.

In the new preparations, the ratio of the anti-hypertensively active aminoacid to a compound of the formula I can vary within substantial limits.

The dosage of the new preparations depends on the activity of the particular active substance components and on the individual requirements of the patient. With the preparations according to the invention, the daily dose of the active substance components can in general be reduced to between about half and about one-third of the customary individual daily dose.

Thus, for example, the abovementioned preparations which have particularly been singled out can contain about 100–200 mg, especially 150–200 mg, of α-amino-α-methyl-β-(3,4-dihydroxyphenyl)-propionic acid and about 50-200 mg, especially 100–200 mg, of the calcium salt of 2-carboxy-4-methoxy-5-n-butyl-pyridine.

The daily dose is about 1-6 such individual doses, which are preferably administered all at once.

The pharmaceutical prepartions according to the invention are mainly suitable for oral or parenteral administration and are preferably in the form of a mixture with a pharmaceutical, organic or inorganic, solid or liquid excipient which is suitable, for example, for enteral or parenteral administration. Possible substances for forming the excipient are those which do not react with the active substances, such as, for example, water, gelatine, lactose, starch, sterile alcohol, magnesium stearate, talc, vegetable oils, benzyl alcohols, gum, propylene glycols, white petroleum jelly or other known medicinal excipients. The pharmaceutical preparations can, for example, be in the form of tablets, dragees, capsules or suppositories or in a liquid form as solutions (for example as an elixir or syrup), suspensions or emulsions. They are optionally sterilised and/or contain auxiliaries, such as preservatives, stabilisers, wetting agents or emulsifiers, solubilising agents or salts for regulating the osmotic pressure or buffers. They can also contain other therapeutically valuable substances. The pharmaceutical preparations are formulated according to customary methods.

The invention is explained with the aid of the examples which follow without this being intended in any way to restrict the scope of the invention.

EXAMPLE 1

50 g (0.188 mol.) of 2-styryl-4-methoxy-5-n-butyl-pyridine are dissolved in 750 ml of acetone and the mixture is cooled to −20° C by means of chloroform-carbon dioxide cooling. 59.5 g (0.376 mol) of potassium permanganate are added over the course of 1 hour at about −15° C. After the complete addition, a resinous, brown-black, very viscous paste is obtained, which can again be made easily stirrable when diluted with about 250 ml of acetone. The reaction mixture is then additionally stirred for 1 hour at −10° C and 2 hours at room temperature. The resulting dark-coloured suspension is evaporated to dryness at 30° C. The resulting residue is twice extracted by boiling with 1 liter of water at a time. The filtrates are concentrated to approx. 100 ml of solution and rendered acid with 300 ml of 2 N sulphuric acid, and the benzoic acid formed is extracted with twice 500 ml of ether.

Th aqueous acid phase is adjusted to exactly pH 5 with sodium hydroxide solution. The brown oil which precipitates is extracted with methylene chloride. The methylene chloride solution is dried and evaporated. The residue is taken up in methanol and twice boiled up with animal charcoal. The filtrate is rendered strongly acid with hydrochloric acid in ether. The reaction mixture is evaporated and all adhering hydrochloric acid, and the water, are driven off by means of toluene. The residue is recrystallised from isopropanol. The resulting compound, 2-carboxy-4-methoxy-5-n-butyl-pyridine hydrochloride, has the formula

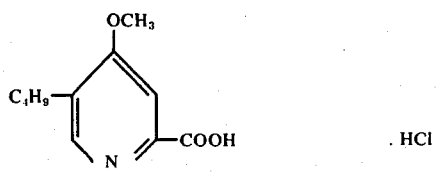
. HCl and has a melting point of 177°/260°. The calcium salt is obtained from this compound by reaction with the calculated amount of calcium hydroxide.

2-Styryl-4-methoxy-5-butyl-pyridine, used as the starting substance, is manufactured in the customary manner, for example by dissolving 50 g of 2-methyl-4-methoxy-5-butylpyridine in 160 ml of benzaldehyde and adding 176 ml of acetic anhydride. The reaction mixture is heated for 20 hours under reflux. After cooling, it is extracted with 2 N sodium hydroxide solution and with ether. The ether residue is fractionated under reduced pressure. 2-Styryl-4-methoxy-5-butyl-pyridine of boiling point 155°–165° C (0.1 mm Hg) is thus obtained.

EXAMPLE 2

A solution of 30 g of 2-hydroxymethyl-4,6-dichloro-5-n-butyl-pyridine in 200 ml of acetone is added dropwise, whilst stirring, to a solution of 40 g of potassium permanganate in 800 ml of acetone. After completion of the reaction, the mixture is stirred for a further 15 hours. The resulting precipitate is filtered off and well rinsed with acetone. The filter residue is extracted by boiling 6 times with 500 ml of water at a time and the mixture is filtered. The filtrate is concentrated. The resulting crystals are filtered off and recrystallised from methanol/acetone. The resulting compound, the potassium salt of 2-carboxy-4,6-dichloro-5-n-butylpyridine, of the formula

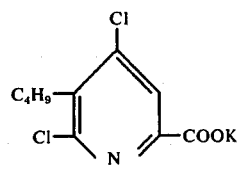

melts at 285°–290° C.

2-Hydroxymethyl-4,6-dichloro-5-butyl-pyridine, used as the starting material, is manufactured as follows:

66 g of 2-methyl-4,6-dichloro-5-n-butyl-pyridine are dissolved in 600 ml of methylene chloride and a solution of 66 g of 85% strength m-chloroperbenzoic acid in 600 ml of methylene chloride is added dropwise over the course of 2½ hours whilst stirring. Thereafter, the mixture is stirred for a further 48 hours at room temperature. The reaction solution is extracted by shaking with aqueous ferrous sulphate solution and with 2 N sodium carbonate solution. The methylene chloride solution is dried and evaporated. 2-Methyl-4,6-dichloro-5-n-butyl-pyridine-N-oxide is thus obtained as the residue. This is taken up in 300 ml of toluene and 82 ml of acetic anhydride are added over the course of 15 minutes whilst stirring. Thereafter the mixture is boiled under reflux for 15 hours. The reaction solution is evaporated. The residue is taken up in ether and extracted by shaking with 2 N sodium carbonate solution. The ether solution is dried and evaporated. After fractionation of the residue, 2-acetoxymethyl-4,6-dichloro-5-n-butyl-pyridine is obtained.

40 g of 2-acetoxymethyl-4,6-dichloro-5-n-butyl-pyridine in 200 ml of 6 N hydrochloric acid are boiled for 15 hours under reflux. Thereafter the mixture is evaporated to dryness. The residue is taken up in chloroform and extracted by shaking with aqueous potassium carbonate solution. The chloroform solution is dried and evaporated. Fractional distillation yields 2-hydroxymethyl-4,6-dichloro-5-n-butyl-pyridine of boiling point 150°–160° (0.1 mm Hg).

EXAMPLE 3

A solution of 32 g (0.14 mol) of 2-hydroxymethyl-4-methoxy-5-n-butyl-6-chloro-pyridine in 500 ml of acetone is added dropwise over the course of one hour to a solution of 44 g (0.28 mol) of potassium permanganate in 750 ml of acetone, at 10° reaction temperature, whilst stirring. After completion of the addition the reaction mixture is stirred for a further hour at 10° and a further 16 hours at about 25°.

The resulting black suspension is evaporated. The residue is extracted by boiling 5 times with 400 ml of water at a time. The water phases are combined and adjusted to pH 4 with 2 N hydrochloric acid. The white crystals which have precipitated are filtered off and dried in a high vacuum at 50°. 2-Carboxy-4methoxy-5-n-butyl-6-chloro-pyridine of the formula

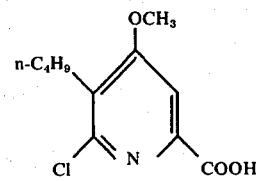

and of melting point 104°–106° is thus obtained.

The starting substance can be manufactured as follows:

A solution of 103 g (0.44 mol) of 2-hydroxymethyl-4,6dichloro-5-n-butyl-pyridine in 100 ml of methanol is added dropwise over the course of 15 minutes, whilst stirring, to a solution of 59.4 g (1.1 mol) of sodium methylate in 500 ml of methanol. After completion of the addition, the reaction mixture is heated for 56 hours under reflux. It is then evaporated to dryness and the residue is suspended in ether. After filtration, the ether filtrate is dried by means of sodium sulphate, filtered and evaporated. Fractional distillation of the residue in a high vacuum yields 2-hydroxymethyl-4-chloro-5-n-butyl-6-methoxy-pyridine of the formula

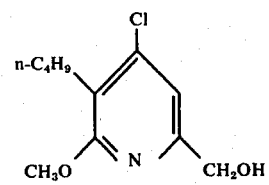

of boiling point 95°–98° (0.06 mm Hg) and 2-hydroxymethyl-4-methoxy-5-n-butyl-6-chloro-pyridine of the formula

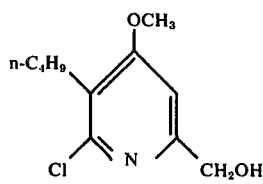

of boiling point 130°–134° (0.03 mm Hg).

EXAMPLE 4

24.3 g (0.1 mol) of 4methoxy-5-n-butyl-6-chloro-2-picolinic acid dissolved in 250 ml of methanol are hydrogenated in the presence of 2.5 g of 5% strength palladium on charcoal. After the calculated amount of hydrogen has been taken up, the catalyst is filtered off and the filtrate is evaporated to dryness. It is freed of the moisture which still adheres, by means of toluene. The white crystals are digested in ether and filtered off. 2-Carboxy-4-methoxy-5-n-butyl-pyridine hydrochloride of the formula

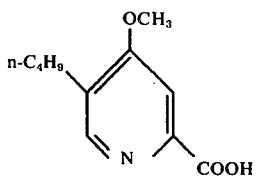

and of melting point 176° is thus obtained.

EXAMPLE 5

A solution of 32 g (0.14 mol) of 2-hydroxymethyl-4-chloro-5-n-butyl-6-methoxy-pyridine in 500 ml of acetone is added dropwise over the course of one hour, whilst stirring at 10° internal temperature, to a solution of 44 g (0.28 mol) of potassium permanganate in 750 ml of acetone. After completion of the addition, the reaction mixture is stirred for a further hour at 10° and a further 16 hours at about 25°. The resulting black suspension is filtered and the residue is well rinsed with acetone.

The filter residue is extracted by boiling 5 times with 500 ml of water at a time and in each case the mixture is filtered hot. The filtrates are combined and adjusted to pH 4 with hydrochloric acid, and the suspension is concentrated to about 500 ml. The crystals which have precipitated are extracted with ether. The ether phases are dried with sodium sulphate and evaporated. The residue is recrystallised from ether-hexane and 2-carboxy-4-chloro-5-n-butyl-6-methoxypyridine of the formula

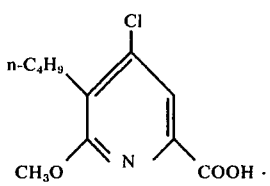

and of melting point 96°–98° is thus obtained.

EXAMPLE 6

2.43 g (0.01 mol) of 4-chloro-5-n-butyl-6-methoxy-2-picolinic acid dissolved in 50 ml of methanol are hydrogenated in the presence of 300 mg of 5% strength palladium on charcoal. After the calculated amount of hydrogen has been taken up, the catalyst is filtered off and the filtrate is evaporated to dryness. Distillation of the residue in a bulb tube in a high vacuum at 120° yields 2-methoxycarbonyl-5-butyl-6-methoxy-pyridine of the formula

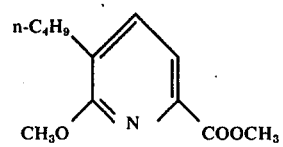

EXAMPLE 7

2.43 g (0.01 mol) of 4-chloro-5-n-butyl-6-methoxy-2-picolinic acid dissolved in 50 ml of 70% strength aqueous methanol are hydrogenated in the presence of 300 mg of 5% strength palladium on charcoal. After the calculated amount of hydrogen has been taken up the catalyst is filtered off and the filtrate is evaporated to dryness. The residue is freed of hydrochloric acid which still adheres, by means of toluene. It is recrystallised from ether-petroleum ether and 2-carboxy-5-n-butyl-6-methoxy-pyridine of the formula

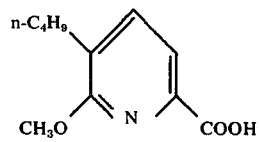

of melting point 73°–74° is thus obtained.

EXAMPLE 8

A solution of 19.7 g (0.07 mol) of 2-hydroxymethyl-4-chloro-5-n-butyl-6piperidino-pyridine in 200 ml of acetone is added dropwise over the course of one hour, whilst stirring at 10° internal temperature, to a solution of 32 g (0.2 mol) of potassium permanganate in 400 ml of acetone. After the addition is complete, the reaction mixture is stirred for a further hour at 10° and a further 16 hours at about 25°. The resulting suspension is filtered off and the residue is well rinsed with acetone. The filter residue is extracted by boiling 5 times with 400 ml of water at a time and the mixture is in each case filtered hot. The filtrates are combined, rendered acid with hydrochloric acid and evaporated to dryness. The amorphous residue is dissolved in methanol and the potassium chloride is filtered off. The methanol filtrate is evaporated. The residue is dissolved in a 5-fold amount of 10 N hydrochloric acid in methanol and the solution is heated under reflux for 8 hours. It is then evaporated to dryness. The residue is rendered alkaline with saturated bicarbonate solution and extracted with ether. The ether phases are combined, dried with sodium sulphate, filtered and evaporated.

The residue is recrystallized from ether-petroleum ether and 2-methoxycarbonyl-4-chloro-5-n-butyl-6-amino-pyridine of the formula

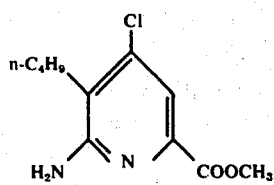

of melting point 125° is thus obtained.

The starting substance can be manufactured as follows:

46.8 g (0.2 mol) of 2-hydroxymethyl-4,6-dichloro-5-n-butyl-pyridine dissolved in 425 g (5 mols) of piperidine are heated for 20 hours at 190° in a bomb tube. The reaction mixture is then evaporated and the piperidine which still adheres is distilled off by means of toluene. The residue is rendered alkaline with 2 N sodium carbonate solution and the mixture is extracted with ether. The ether phases are combined, dried over sodium sulphate, filtered and evaporated. Fractional distillation of the residue in a high vacuum yields 2-hydroxymethyl-4-chloro-5-n-butyl-6-piperidino-pyridine of the formula

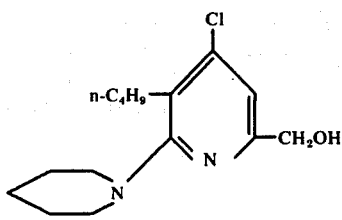

and of boiling point 147°–152° (0.25 mm Hg).

EXAMPLE 9

1 g of 4-chloro-5n-butyl-6-amino-2-picolinic acid methyl ester dissolved in 10 ml of methanol is hydrogenated in the presence of 100 mg of 5% strength palladium on charcoal. After the calculated amount of hydrogen has been taken up the catalyst is filtered off and the filtrate is evaporated to dryness. The residue is rendered alkaline with saturated sodium bicarbonate solution and extracted with ether. The ether phases are combined, dried over sodium sulphate and evaporated. The residue is recrystallised from ether-petroleum ether and 2-methoxycarbonyl-5-n-butyl-6-amino-pyridine of the formula

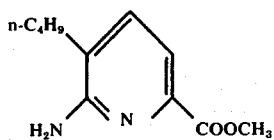

and of melting point 81°–82° is thus obtained.

EXAMPLE 10

100 ml of 10 N hydrochloric acid in methanol are added to a solution of 19.7 g (0.08 mol) of 4-methoxy-5-n-butyl-2l -picolinic acid hydrochloride in 200 ml of methanol and the mixture is heated for 6 hours under reflux. It is then evaporated to dryness. The residue is rendered alkaline with saturated sodium bicarbonate solution and the mixture is extracted with ether. The ether phases are combined, dried with sodium sulphate, filtered and evaporated. Distillation of the residue in a bulb tube at a temperature of 160°–180° and at 0.3 mm Hg yields 2-methoxycarbonyl-4-methoxy-5-n-butyl-pyridine of the formula

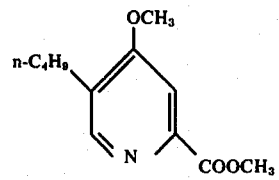

EXAMPLE 11

11.15 g (0.05 mol) of 4-methoxy-5-n-butyl-2-picolinic acid methyl ester and 220 ml of a 33% strength solution of ammonia in methanol are heated in a bomb tube for 18 hours to 70°. The reaction mixture is evaporated and the amorphous residue is recrystallised from ether. The crystals are dissolved in methanol and the solution is rendered acid with hydrochloric acid in methanol. The acid solution is evaporated and dried by means of toluene. The crystals are digested in acetone. After cooling, they are filtered off. 2-Carbamoyl-4-methoxy-5-n-butyl-pyridine hydrochloride of the formula

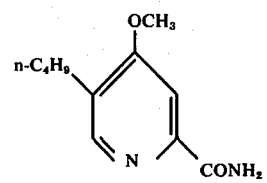

and of melting point 159°–162° is thus obtained.

EXAMPLE 12

53.5 (0.338 mol) of potassium permanganate are dissolved in 600 ml of acetone and the solution is cooled to 10°. At this temperature, 33.4 g (0.113 mol) of 2-styryl-4-n-propoxy-5-n-butyl-pyridine in 200 ml of acetone are added dropwise over the course of 1 hour. The reaction mixture is subsequently stirred for a further hour at 10° and a further 16 hours at about 25°. The resulting almost black suspension is filtered and the residue is well rinsed with acetone. The filter residue is extracted by boiling 5 times with 300 ml of water at a time and the mixture is in each case filtered hot. The filtrates are combined, adjusted to pH=1 with 2 N sulphuric acid and concentrated to about 500 ml. The benzoic acid formed is extracted with twice 300 ml of ether.

The aqueous acid phase is adjusted to pH=5 with 2 N sodium hydroxide solution. The oil which has precipitated is extracted with methylene chloride. The methylene chloride phases are combined, dried over sodium sulphate, filtered and evaporated. The residue is taken up in methanol and rendered strongly acid with hydrochloric acid in ether. The acid solution is evaporated. The residue is taken up in isopropanol, boiled up with animal charcoal and filtered. The filtrate is evaporated and dried by treatment with toluene.

The residue thus obtained is digested with benzene. 2-Carboxy-4-n-propoxy-5-n-butyl-pyridine hydrochloride of the formula

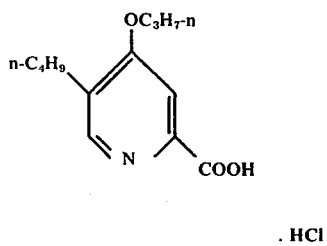

. HCl and of melting point 156°–158° is thus obtained.

The starting substance can be manufactured as follows:

22.6 g of 4-n-propoxy-5-n-butyl-2-picoline and 60 ml of benzaldehyde are heated with 66 ml of acetic anhydride for 16 hours under reflux. After cooling, the mixture is evaporated, 2 N sodium hydroxide solution is added and the whole is extracted with ether. Distillation of the ether residue in a bulb tube at a temperatre of 160°–180° in a high vacuum yields 2-styryl-4-n-propoxy-5-n-butyl-pyridine.

EXAMPLE 13

43.5 g (0.28 mol) of potassium permanganate are dissolved in 500 ml of acetone and the solution is cooled to 10°. At this temperature, 26.0 g (0.093 mol) of 2-sytryl-4-methoxy-5-isoamyl-pyridine dissolved in 250 ml of acetone are added dropwise over the course of 1 hour. After the complete addition, a brown-black suspension has been formed. The reaction mixture is then further stirred for 1 hour at 10° and a further 16 hours at about 25°. The resulting almost black suspension is filtered and the residue is well rinsed with acetone. The filter residue is extracted by boiling 5 times with 400 ml of water at a time and is in each case filtered hot. The filtrates are combined, rendered acid with 2 N sulphuric acid and concentrated to approx. 500 ml. The benzoic acid formed is extracted with twice 300 ml of ether.

The aqueous acid phase is adjusted to pH=5 with 2 N sodium hydroxide solution. The oil which has precipitated is extracted 5 times with 300 ml of methylene chloride at a time. The methylene phases are combined, dried over sodium sulphate, filtered and evaporated. The residue is recrystallised from ether. 2-Carboxy-4-methoxy-5-isoamylpyridine hemihydrate of the formula

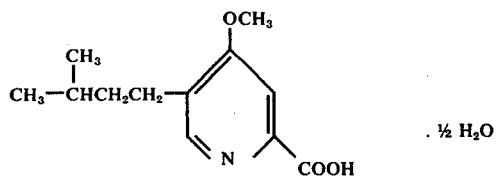

. ½ H₂O and of melting point 146°–147° (with decomposition) is thus obtained.

The starting substance can be manufactured by dissolving 26 g of 4-methoxy-5-isoamyl-2-picoline in 78 ml of benzaldehyde and 86 ml of acetic anhydride and heating the reaction mixture for 16 hours under reflux. After cooling, the mixture is evaporated, treated with 2 N sodium hydroxide solution and extracted with ether. Distillation of the ether residue in a bulb tube in a high vacuum at a temperature of 180°–200° yields 2-styryl-4-methoxy-5-isoamyl-pyridine.

EXAMPLE 14

34.8 g (0.22 mol) of potassium permanganate are dissolved in 300 ml of acetone and the solution is cooled to 10°. At this temperature, 20.5 g (0.073 mol) of 2-styryl-4-methoxy-5-n-amyl-pyridine dissolved in 200 ml of acetone are added dropwise over the course of 1 hour. After the complete addition, a brown-black suspension has been formed. The reaction mixture is then further stirred for 1 hour at 10° and a further 16 hours at about 25°. The resulting almost black suspension is filtered and the residue is well rinsed with acetone. The filter residue is extracted 5 times by boiling with 300 ml of water at a time and the mixture is in each case filtered hot. The filtrates are combined, acidified with 2 N sulphuric acid and concentrated to about 500 ml. The benzoic acid formed is extracted with twice 300 ml of ether.

The aqueous acid phase is adjusted to pH=5 with 2 N sodium hydroxide solution. The oil which has precipitated is extracted 5 times with 300 ml of methylene chloride at a time. The methylene chloride phases are combined, dried over sodium sulphate, filtered and evaporated. The residue is recrystallised from ether and 2-carboxy-4-methoxy-5-n-amyl-pyridine of the formula

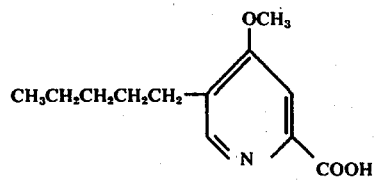

and of melting point 127°–128° is thus obtained.

The starting substance can be manufactured as follows:

23.3 g of 4-methoxy-5-n-amyl-2-picoline and 70 ml of benzaldehyde are heated with 77 ml of acetic anhydride for 16 hours under reflux. After cooling, the mixture is evaporated and the residue is treated with 2 N sodium hydroxide solution and extracted with ether. Distillation of the ether residue in a bulb tube in a high vacuum at a temperature of 180°–200° yields 2-styryl-4-methoxy-5-n-amyl-pyridine.

EXAMPLE 15

109 g (0.69 mol) of potassium permanganate are dissolved in 1,000 ml of acetone and the solution is cooled to 10°. At this temperature, 64.5 g (0.23 mol) of 2-styryl-4-ethoxy-5-n-butyl-pyridine dissolved in 300 ml of acetone are added dropwise over the course of 1 hour. After the complete addition, a brown-black suspension has been formed. The reaction mixture is then stirred for a further hour at 10° and a further 16 hours at about 25°. The resulting almost black suspension is filtered and the residue is well rinsed with acetone. The filter residue is extracted by boiling 5 times with 400 ml of water at a time and in each case the mixture is filtered hot. The filtrates are combined, acidified with 2 N sulphuric acid and concentrated to about 500 ml. The benzoic acid formed is extracted with twice 400 ml of ether.

The aqueous acid phase is adjusted to pH=5 with 2 N sodium hydroxide solution. The oil which has precipitated is extracted 5 times with 400 ml of methylene chloride at a time. The methylene chloride phases are combined, dried over sodium sulphate, filtered and evaporated. The residue is taken up in methanol and the solution is rendered strongly acid with hydrochloric acid in ether. The acid solution is evaporated. The residue is taken up in isopropanol and the mixture is twice boiled up with animal charcoal and filtered. The filtrate is evaporated and all adhering hydrochloric acid, and the water, are driven off with toluene.

The residue is crystallised from isopropanol-ether and 2-carboxy-4-ethoxy-5-n-butyl-pyridine hydrochloride of the formula

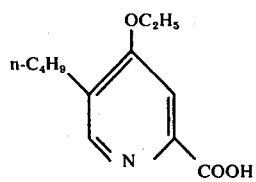

. HCl of melting point 155°–157° (with decomposition) is thus obtained.

The starting substance can be manufactured as follows:

55 g of 4-ethoxy-5-n-butyl-2-picoline and 165 ml of benzaldehyde in 181 ml of acetic anhydride are heated for 16 hours under reflux. After cooling, the mixture is evaporated, and the residue is treated with 2 N sodium hydroxide solution and extracted with ether. Distillation of the ether residue in a bulb tube at a temperature of 160°–180° in a high vacuum yields 2-styryl-4-n-propoxy-5-n-butyl-pyridine.

EXAMPLE 16

A suspension of 28.6 g (0.1 mol) of the potassium salt of 4,6-dichloro-5-n-butyl-2-picolinic acid in 200 ml of 80% strength aqueous methanol is adjusted to pH=5 with hydrochloric acid in methanol. The solution is evaporated to dryness. The water is distilled off azeotropically with toluene. The residue is dissolved in 200 ml of piperidine and heated for 24 hours under reflux whilst stirring. It is then evaporated to dryness and the piperidine which still adheres is removed with toluene. The residue is dissolved in 350 ml of 5 N hydrochloric acid in methanol and the solution is heated under reflux for 8 hours. After evaporation to dryness, the mixture is rendered alkaline with saturated sodium bicarbonate solution and is extracted with ether. The ether phases are combined, dried over sodium sulphate, filtered and evaporated.

Fractional distillation of the ether residue in a high vacuum at 180°–200° yields 2-methoxy-carbonyl-4-piperidino-5-n-butyl-6-chloro-pyridine of the formula

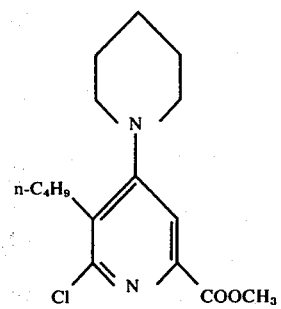

EXAMPLE 17

14 g (0.045 mol) of 4-piperidino-5-n-butyl-6-chloro-2-picolinic acid methyl ester, dissolved in 140 ml of methanol, are hydrogenated in the presence of 1.4 g of palladium on charcoal. After the calculated amount of hydrogen has been taken up, the catalyst is filtered off and the filtrate is evaporated to dryness. It is freed by means of toluene of the moisture which still adheres. The residue is recrystallised from acetone-ether. 2-Methoxy-carbonyl-4-piperidino-5-n-butyl-pyridine hydrochloride of the formula

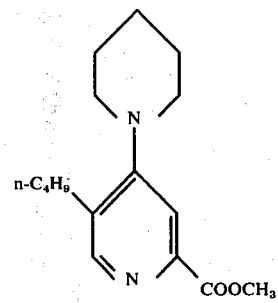

. HCl and of melting point 123°–125° is thus obtained.

EXAMPLE 18

25.0 g of 2-acetoxymethyl-4-methoxy-5-n-butyl-pyridine dissolved in 250 ml of 6 N hydrochloric acid are heated for 10 hours under reflux. After evaporation to dryness in vacuo, the residue is treated with 250 g of ice, rendered alkaline with concentrated aqueous ammonia solution and extracted with ether. The ether phases are combined, dried with sodium sulphate, filtered and evaporated. Distillation of the residue in a bulb tube at 0.5 mm Hg and 120° yields 2-hydroxymethyl-4-methoxy-5-n-butyl-pyridine of the formula

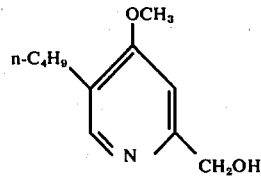

A solution of 2-hydroxymethyl-4-methoxy-5-n-butyl-pyridine in methanol is adjusted to pH 1 with hydrochloric acid in ether and evaporated to dryness. The water which still adheres is distilled off azeotropically with toluene. The residue thus obtained is digested with acetone and the crystalline product is filtered off. 2-Hydroxymethyl-4-methoxy-5-n-butyl-pyridine hydrochloride of melting point 136°–137° is thus obtained.

The starting material can be obtained as follows:

A solution of 30 g (0.17 mol) of 4-methoxy-5-n-butyl-2-picoline in 350 ml of methylene chloride is added dropwise over the course of 1½ hours, whilst stirring at about 25°, to a solution of 40 g (0.2 mol) of m-chloroperbenzoic acid (approx. 85% strength) in 400 ml. of methylene chloride.

After completion of the addition, the solution is stirred for 48 hours at about 25°. To destroy the excess m-chloroperbenzoic acid, a solution of 75 g of iron-II sulphate in 250 ml of water is added dropwise. The resulting emulsion is vigorously stirred for 30 minutes. The methylene chloride phase is separated off and washed once with water, then twice with 500 ml of 2 N sodium carbonate solution at a time, and once more with water. Thereafter it is dried with sodium sulphate, filtered and evaporated at 35° bath temperature in a water pump vacuum.

4-Methoxy-5-n-butyl-2-picoline-N-oxide is thus obtained.

20.4 g (0.2 mol) of acetic anhydride are added dropwise to a solution of 19.5 g (0.1 mol) of 4-methoxy-5-n-butyl-2-picoline-N-oxide in 100 ml of toluene over the course of 15 minutes, whilst stirring. Thereafter the mixture is heated for 8 hours under reflux. After evaporation to dryness in vacuo, the mixture is rendered alkaline with 2 N aqueous sodium carbonate solution and is extracted with ether. The ether phases are combined, dried with sodium sulphate, filtered and evaporated. Distillation of the residue in a bulb tube in a high vacuum at 120° yields 2-acetoxymethyl-4-methoxy-5-n-butyl-pyridine.

EXAMPLE 19

7.3 g (0.03 mol) of 2-carboxy-4-methoxy-5-n-butyl-6-chloro-pyridine dissolved in 112 g (1.5 mols) of piperidine are heated to 140° in a bomb tube for 12 hours. The reaction mixture is evaporated and the residue is freed of still adhering piperidine by means of toluene. It is recrystallised from acetone and 2-carboxy-4-methoxy-5-n-butyl-6-piperidino-pyridine hydrochloride of the formula

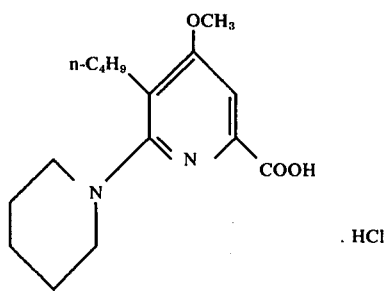

and of melting point 150°–154° is thus obtained.

EXAMPLE 20

28.6 g (0.1 mol) of the potassium salt of 2-carboxy-4,6-dichloro-5-n-butyl-pyridine are added to a saturated solution of 200 g of KOH in 400 ml of methanol. The mixture is heated for 36 hours under reflux. After cooling, it is rendered acid with 6 N hydrochloric acid and extracted with methylene chloride. The methylene chloride phases are combined, dried with sodium sulphate, filtered and evaporated. The residue is crystallised from benzene-petroleum ether. 2-Carboxy-4,6-dimethoxy-5-n-butyl-pyridine of the formula

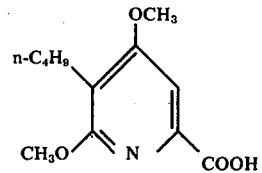

amd of melting point 113°–114° is thus obtained.

EXAMPLE 21

50 ml of 10 N hydrochloric acid in methanol are added to a solution of 12.2 g (0.05 mol) of 2-carboxy-4-chloro-5-n-butyl-6-methoxy-pyridine in 100 ml of methanol and the mixture is heated for 4 hours under reflux. It is then evaporated to dryness and hydrochloric acid which still adheres is distilled off with toluene. The residue is recrystallised from ether and 2-methoxycarbonyl-4-chloro-5-n-butyl6-hydroxy-pyridine of the formula

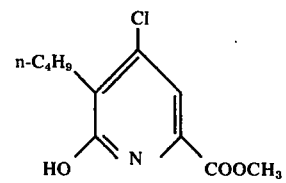

and of melting point 135°–136° is thus obtained.

EXAMPLE 22

Tablets

| Composition | |
|---|---|
| 2-Carboxy-4-methoxy-5-n-butyl-pyridine hydrochloride | 100 mg |
| Lactose | 58 mg |
| Corn starch | 75 mg |
| Colloidal silica | 8 mg |
| Talc | 8 mg |
| Magnesium stearate | 1 mg |
| | 250 mg |

MANUFACTURE

The 2-carboxy-4-methoxy-5-n-butyl-pyridine.HCl is mixed with the lactose, a part of the corn starch and with colloidal silica and the mixture is forced through a sieve. A further part of the corn starch is worked into a paste with a 5-fold amount of water on a water bath and the powder mixture is kneaded with this paste until a slightly plastic mass has been produced.

The plastic mass is forced through a sieve of approx. 3 mm mesh width and dried and the resulting dry granules are again forced through a sieve. Thereafter the remaining corn starch, talc and magnesium stearate are mixed in and the mixture obtained is pressed to give tablets weighing 250 mg (having a breaking groove), and containing 100 mg of the active compounds.

EXAMPLE 23

Tablets

| Composition | |
|---|---|
| Ca salt of 2-carboxy-4-methoxy-5-n-butyl-pyridine | 300 mg |
| Lactose | 66 mg |
| Corn starch | 100 mg |
| Colloidal silica | 16 mg |
| Talc | 16 mg |
| Magnesium stearate | 2 mg |
| | 500 mg |

MANUFACTURE

The calcium salt of 2-carboxy-4-methoxy-5-n-butyl-pyridine is mixed with the lactose, a part of the corn starch and with colloidal silica and the mixture is forced through a sieve. A further part of the corn starch is worked into a paste with a 5-fold amount of water on a water bath and the powder mixture is kneaded with this paste until a slightly plastic mass has been produced.

The plastic mass is forced through a sieve of approx. 3 mm mesh width and dried and the resulting dry granules are again forced through a sieve. Thereafter the remaining corn starch, talc and magnesium stearate are mixed in and the mixture obtained is pressed to give tablets weighing 500 mg (having a breaking groove), and containing 300 mg of the active compound.

EXAMPLE 24

Tablets containing 200 mg of α-methyldopa and 300 mg of the calcium salt of 2-carboxy-4-methoxy-5-n-butyl-pyridine:

| Composition | |
|---|---|
| α-Methyldopa | 200 mg |
| Calcium salt of 2-carboxy-4-methoxy-5-n-butyl-pyridine | 300 mg |
| Lactose | 41 mg |
| Wheat starch | 75 mg |
| Colloidal silica | 16 mg |
| Talc | 16 mg |
| Magnesium stearate | 2 mg |
| | 650 mg |

MANUFACTURE

The α-methyldopa and the calcium salt of 2-carboxy-4-methoxy-5-n-butyl-pyridine are mixed with the lactose, a part of the wheat starch and with colloidal silica and the mixture is forced through a sieve. A further part of the wheat starch is worked into a paste with a 5-fold amount of water on a water bath and the powder mixture is kneaded with this paste until a slightly plastic mass has been produced.

The plastic mass is forced through a sieve of approx. 3 mm mesh width and dried and the dry granules are again forced through a sieve. Thereafter the remaining wheat starch, talc and magnesium stearate are mixed in and the mixture obtained is pressed to give tablets weighing 650 mg (with a breaking groove).

EXAMPLE 25

300 ml of 5 N hydrochloric acid in methanol are added to 28.6 g (0.1 mol) of the potassium salt of 2-carboxy-4,6-dichloro-5-n-butyl-pyridine and the mixture is heated for 8 hours under reflux. It is then evaporated to dryness and hydrochloric acid which still adheres is distilled off with toluene. The residue is rendered alkaline with 2 N sodium carbonate solution and extracted with ether. The ether phases are combined, dried with sodium sulphate and evaporated. Distillation of the residue in a bulb tube at a temperature of 140°–160° at 0.3 mm Hg yields 2-methoxycarbonyl-4,6-dichloro-5-n-butyl-pyridine of the formula

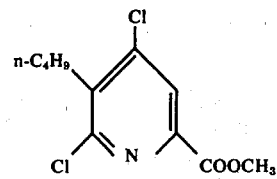

EXAMPLE 26

13.1 g (0.05 mol) of 2-methoxycarbonyl-4,6-dichloro-5-n-butyl-pyridine in 100 g of liquid ammonia are heated to 180° for 20 hours in an autoclave. The reaction mixture is evaporated and the residue is twice extracted by boiling with 150 ml of ethyl acetate at a time and in each case the mixture is filtered hot. The combined ethyl acetate extracts are concentrated to a volume of approx. 50 ml and treated with ether. The isomer mixture is 2-carbamoyl-4-amino-5-n-butyl-6-chloro-pyridine and 2-carbamoyl-4-chloro-5-n-butyl-6-amino-pyridine of the formula

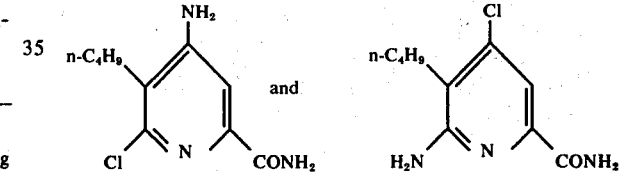

and of melting point 160°–180° thus crystallises.

EXAMPLE 27

11.4 g (0.05 mol) of the isomer mixture of 2-carbamoyl-4-amino-5-n-butyl-6-chloro-pyridine and 2-carbamoyl-4-chloro-5-n-butyl-6-amino-pyridine, dissolved in 120 ml of pure methanol, are hydrogenated in the presence of 1.5 g of palladium on charcoal. After the calculated amount of hydrogen has been taken up, the catalyst is filtered off and the filtrate is evaporated to dryness. The residue is rendered alkaline with 2 N sodium carbonate solution and extracted with ether. The crystalline product which is soluble in neither sodium carbonate solution nor in ether is filtered off and rinsed with water. The white crystals are dried for 20 hours at 70° in a high vacuum. 2-Carbamoyl-4-amino-5-n-butyl-pyridine of the formula

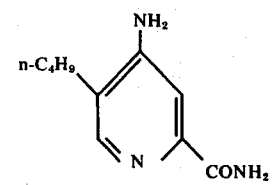

and of melting point 186°–190° is thus obtained.

The ether extracts are combined, dried with sodium sulphate and evaporated. The residue is recrystallised from ether and 2-carbamoyl-5-n-butyl-6-amino-pyridine of the formula

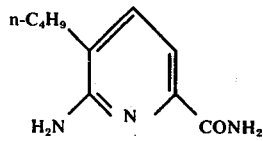

and of melting point 103°–105° is thus obtained.

What we claim is:

1. A pharmaceutical preparation useful in the treatment of hypertension, which comprises an antihypertensively effective amount of a compound of the formula

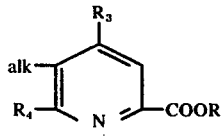

in which R represents hydrogen or lower alkyl, alk represents an alkyl group having 4 to 5 carbon atoms, $R_3$ and $R_4$ each represents chloro or lower alkoxy and one of the symbols $R_3$ and $R_4$ may also represent hydrogen or a therapeutically usable salt thereof, together with a therapeutically usable excipient.

2. The pharmaceutical preparation of claim 1, wherein the active compound is 2-carboxy-4-methoxy-5-n-butyl-pyridine or a therapeutically usable salt thereof.

3. A pharmaceutical preparation useful for the treatment of hypertension, which comprises an antihypertensively effective amount of a combination of a compound of the formula

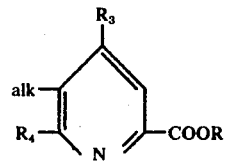

in which R represents hydrogen or lower alkyl, alk represents an alkyl group having 4 to 5 carbon atoms, $R_3$ and $R_4$ each represents chloro or lower alkoxy and one of the symbols $R_3$ and $R_4$ may also represent hydrogen or a therapeutically usable salt thereof together with a therapeutically usable excipient and an antihypertensively active amino acid together with a therapeutically usable excipient.

4. The preparation of claim 3 wherein the amino acid is an α-methyldopa type compound.

5. The preparation of claim 4 wherein said amino acid is α-amino-α-methyl-B-hydroxypropionic acid or a pharmaceutically acceptable salt or ester thereof.

6. The preparation of claim 1 wherein said compound is 2-carboxy-4-methoxy-5-n-butyl pyridine or a non-toxic salt thereof and said amino acid is α-amino-α-methyl-β-(3,4-dihydroxy phenyl)-propionic acid or an alkali metal or alkaline earth metal salt thereof.

7. The preparation of claim 4 containing 100 to 200 mg of α-amino-α-methyl-β-(3,4-dihydroxy phenyl)-propionic acid and 50 to 200mg of the calcium salt of 2-carboxy-4-methoxy-5-n-butyl-pyridine.

* * * * *